US006337184B1

(12) United States Patent
Miller

(10) Patent No.: US 6,337,184 B1
(45) Date of Patent: *Jan. 8, 2002

(54) MOLECULAR MARKER FOR MUSCLE STEM CELLS

(76) Inventor: Jeffrey B. Miller, 245 Concord Ave., #16, Cambridge, MA (US) 02138

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/053,031

(22) Filed: Apr. 1, 1998

Related U.S. Application Data

(60) Provisional application No. 60/041,825, filed on Apr. 1, 1997.

(51) Int. Cl.$^7$ ............................. C12Q 1/68; C12N 5/08; C12N 15/85; C07H 21/04

(52) U.S. Cl. ......................... 435/6; 435/377; 435/455; 536/23.1; 536/24.1

(58) Field of Search ........................... 435/6, 377, 455; 536/23.1, 24.1

(56) References Cited

U.S. PATENT DOCUMENTS

| | | | |
|---|---|---|---|
| 5,015,568 A | 5/1991 | Tsujimoto et al. | |
| 5,202,429 A | 4/1993 | Tsujimoto et al. | |
| 5,328,695 A | 7/1994 | Lucas et al. | 424/426 |
| 5,466,676 A | * 11/1995 | Booth et al. | 514/44 |
| 5,484,710 A | 1/1996 | Reed et al. | 435/69.1 |
| 5,539,085 A | 7/1996 | Bischoff et al. | |
| 5,550,019 A | 8/1996 | Reed | |
| 5,602,301 A | 2/1997 | Field | 800/8 |
| 5,789,389 A | * 8/1998 | Tarasewicz et al. | 514/44 |

FOREIGN PATENT DOCUMENTS

WO WO 96/38544 12/1996

OTHER PUBLICATIONS

Hockenbery et al.; "BLC2 Protein is Topographically Restricted in Tissues Characterized by Apoptotic Cell Death"; Proc. Natl. Acad. Sci., vol. 88:6961–6965, Cell Biology, Aug. 1991.

Lu et al.; "BCL–2 Expression in Adult and Embryonic Non–Hematopoietic Tissues"; Journal of Pathology, vol. 169:431–437 (1993).

Young et al.; "A Negative Regulatory Element in the bcl–2 5'–Untranslated Region Inhibits Expression from an Upstream Promoter"; Mol. and Cell. Biology, Jun. 1993 pp. 3686–3697.

Miyashita et al; "Identification of a P53–Dependent Negative Response Element in the bcl–2 Gene", Cancer Research vol. 54:3131–3135; Jun. 15, 1994.

Hesketh; "Oncogene Factsbook"; Academic, London, GB; pp. 52–56; 1995.

Dony et al; "An Embryonal Carcinoma Cell Line as a Model System to Study Developmentally Regulated Genes During Myogenesis", Cell Differentiation, vol. 15:275–279; 1984.

"Age–Dependent Changes in Myogenic Precursor Cell Compartment Sizes"; Quinn et al.; Experimental Cell Research, vol. 154, No. 1, Sep. 1984, pp. 65–82.

"Identification of self–renewing myoblasts in the progeny of single human muscle satellite cells"; Baroffio et al.; Differentiation 60, 1996, pp. 47–57.

"Characterization of the protein product of blc–2, the gene involved in human follicular lymphoma"; Tsujimoto et al.; Oncogene, vol. 2, No. 1, 1987, pp. 3–7.

"Analysis of the structure, transcripts, and protein products . . . lymphoma"; Tsujimoto et al.; Proc. Natl. Acad. Sci., USA, vol. 83, Jul. 1986, pp. 5216–5218.

"Regulations of cell death"; Korsmeyer; Trends in Genetics, DNA, Differentiation & Development; Reference Edition, vol. 11, 1995, pp. 101–105.

"Investigation of the Subcellular Distribution of the bcl–2 . . . membranes"; Krajewski et al.; Cancer Research, vol. 53, No. 19, Oct. 1, 1993, pp. 4701–4714.

"bCL–2–Deficient Mice Demonstrate Fulminant Lymphoid . . . Hypopigmented Hair"; Veis et al.; Cell, vol. 75. No. 2, Oct. 22, 1993, pp. 229–240.

"π1 Binding Sites Are Negative Regulators of blc–2 Expression in Pre–B Cells"; Chen; Molecular and Cellular Biology , Jul. 1995, pp. 3840–3847.

"Taxol Induces blc–2 Phosphorylation and Death of Prostate Cancel Cells"; Haldar et al.; Cancer Research vol. 56, No. 6, Mar. 15, 1996, pp. 1179–1469.

"Molecular Analysis of mbcl–2: Structure and Expression of the Murine . . . Lympoma"; Negrini et al.; Cell, vol. 49, May 22, 1987, pp. 455–463.

"Myogenic Programs of Mouse Muscle Cell Lines: Expression of Myosin Heavy Chain Isoforms, MyoD1, and Myogenin"; Miller; The Journal of Cell Biology, vol. III, No. 3, Sep. 1990, pp. 1149–1159.

"Myogenesis and the Intermediate Filament Protein, Nestin"; Kachinsky et al.; Development Biology, vol. 165, No. 1, Sep. 1994, pp. 216–228

"A unique pattern of expression of the four muscle regulatory factor . . . myogenic cells"; Smith et al; Development, vol. 117(3), Mar. 1993; pp. 1125–1133.

"In Vitro and in Vivo Expression of α7 Integrin and Desmin . . . Myogenic Lineages"; George–Weinstein et al.; Developmental Biology, vol. 156, 1993, pp. 209–229.

(List continued on next page.)

*Primary Examiner*—Terry McKelvey
*Assistant Examiner*—William Sandals
(74) *Attorney, Agent, or Firm*—Fish & Richardson, P.C.

(57) ABSTRACT

In accordance with the invention, Bcl-2 expression is a molecular marker for muscle stem cells. Thus, the invention provides methods for identifying and isolating muscle stem cells. In addition, the invention provides methods for determining whether a test compound modulates muscle stem cell differentiation and/or proliferation. Finally, the invention provides methods for expressing an exogenous coding sequence in a muscle stem cell.

17 Claims, 5 Drawing Sheets-

OTHER PUBLICATIONS

Okta et al, Up–regulated expression of Murine Mell/FzAT, A Bel–z related gene, in the early stage of differentiation of murine embryonal carcinoma cells and embryonic stem cells Biochim, Biophys. ACTA vol. 1398:335–341, 1998.*

Baroffio et al. Identification of self–renewing myoblasts in the progeny of single human muscle satellite cells. Differentiation vol. 60:47–57, Jan. 1996.*

Lichnovsky et al. Expression des BCL–2 proteins in den geeben und organen menschlicher keimlinge. ACTA Univ. Palacki. Olomuc. vol. 140:39–41, Jun. 1996.*

Pari et al. Multiple CArG boxes in the human cardiac actin gene promoter required for expression in embryonic cardiac muscle cells developing in vitro from embryonal carcinoma cells. Mol. and Cellullar Biol. vol. 11(9):4796–4803, Sep. 1991.*

Dinsmore et al. Embryonic stem cells differentiated in vtro as a novel source of cells for transplantation. Cell Transplantation. vol. 5(2):131–143, Jan. 1996.*

Wobus et al. In vitro differentiation of embryonic stem cells into cardiomyocytes or skeletal muscle cells is specifically modulated by retinoic acid. Roux's Arch. Dev. Biol. vol. 204:36–45, Jan. 1994.*

* cited by examiner

MOLECULAR MARKER FOR MUSCLE STEM CELLS

Under 35 U.S.C. §119(e) (1), this application claims the benefit of prior U.S. provisional application No. 60/041,825, filed Apr. 1, 1997.

STATEMENT AS TO FEDERALLY SPONSORED RESEARCH

This invention was made, at least in part, with funds provided by the United States government through National Institutes of Health grant 1RO1AR43565, and the United States government therefore has certain rights in the invention.

BACKGROUND OF THE INVENTION

The field of the invention is molecular markers for muscle stem cells.

The development, growth, and repair of skeletal muscles all require mononucleate myoblasts that are committed to form multinucleate myofibers via intercellular fusion. Committed myoblasts are thought to be the progeny of uncommitted, self-renewing stem cells; however, molecular markers that would permit identification and study of muscle stem cells have not previously been described (Quinn et al., Exp. Cell Res. 154, 65–82 (1984); Baroffio et al., Differentiation 60, 47–57 (1996)). These and all other publications and patents cited herein are hereby incorporated by reference.

SUMMARY OF THE INVENTION

It has now been discovered that Bcl-2, an apoptosis-inhibiting protein, is expressed in muscle stem cells, but not in other myogenic cells (e.g., multinucleate myotubes and myofibers). Thus, Bcl-2 is a molecular marker for muscle stem cells (e.g., human muscle stem cells). This discovery suggests a number of methods for identifying and/or isolating muscle stem cells. For example, one method of the invention provides a means for identifying a muscle stem cell by providing a sample that includes a myogenic cell and detecting activity of a Bcl-2 promoter within the myogenic cell as an indication that the myogenic cell is a muscle stem cell. The invention can be used to detect muscle stem cells that produce skeletal muscle, smooth muscle, or cardiac muscle. The Bcl-2 marker also can be used to detect and characterize a stem cell component in muscle tumors (e.g., in methods of diagnosing or evaluating muscle tumors).

The activity of the Bcl-2 promoter can be detected by any of a variety of methods. For example, the activity of the Bcl-2 promoter can be detected by detecting a Bcl-2 protein in the myogenic cell. To this end, conventional methods, such as SDS-PAGE and/or immunoassays, can be employed. Antibodies that specifically bind Bcl-2 are known in the art and readily available for use in such immunoassays. If desired, the activity of the Bcl-2 promoter can be detected by detecting Bcl-2 mRNA in the myogenic cell. Art-known methods such as reverse transcription-PCR (RT-PCR), in situ hybridization, and Northern blots can be used to detect the Bcl-2 mRNA.

In a variation of the above methods, the activity of a Bcl-2 promoter is detected with the use of a heterologous reporter gene (e.g., a chloramphenicol acetyltransferase gene, an alkaline phosphatase gene, a luciferase gene, or a green fluorescent protein gene). In a typical method, the heterologous reporter gene is operably linked to a Bcl-2 promoter in a genetic construct (e.g., a viral-based vector or a plasmid). Conventional molecular biology techniques can be used to produce such a genetic construct. The genetic construct then is introduced into a population of cells containing myogenic cells and thought to contain muscle stem cells. Since no myogenic cells except muscle stem cells activate the Bcl-2 promoter, expression of the reporter gene is detected as an indication that a cell is a muscle stem cell. As above, conventional methods for detecting gene expression can be used to detect reporter gene expression (e.g., protein or mRNA assays).

Now that a molecular marker for identifying muscle stem cells has been discovered, several related methods are possible. Thus, the invention also provides a method for determining whether a test compound(s) modulates muscle stem cell differentiation. In this method, a cell is identified as a muscle stem cell (e.g., by using one of the abovedescribed methods). The muscle stem cell is contacted with the test compound (e.g., in vitro). A change in the differentiation of the stem cell, compared to control, is an indication that the compound modulates muscle stem cell differentiation. Any compound can be used as the test compound in this method. Both naturally-occurring and synthetic polypeptides and small organic molecules are suitable test compounds. Compounds and analogs of compounds that are known to affect the differentiation of other cells are particularly suitable for use in this method. Parameters such as the rate and pattern of cell differentiation can be measured using conventional means. In a related method, one can determine whether a test compound modulates muscle stem cell proliferation. This method is nearly identical to that described above, except that a change in cell proliferation, compared to control, is detected. Of particular interest are test compounds that modulate the rate of cell proliferation. Of course, the above-described methods for detecting compounds that modulate cell differentiation and proliferation can be combined into a single experiment using one or more test compounds.

The invention also provides a method for producing a population of cells that is enriched for muscle stem cells relative to a reference population of cells. The method entails providing a reference population of cells that includes a plurality of muscle stem cells and at least one cell (typically many cells) other than a muscle stem cell (e.g., myoblasts). Typically, the reference population is obtained by muscle biopsy. A genetic construct may be introduced into the reference population of cells. The genetic construct includes a Bcl-2 promoter that is operably linked to a gene encoding a marker protein. The marker protein is a protein that is heterologous to wild-type cells of the reference population. Cells that express the marker protein (i.e., cells in which the Bcl-2 promoter is active) are then isolated in order to produce a population of cells enriched for muscle stem cells. Of course, by removing the Bcl-2-expressing cells from the cell population, this method can be used to produce a population of cells depleted of muscle stem cells.

The heterologous marker protein can be viral, prokaryotic, eukaryotic, or synthetic in origin. Preferably, the marker protein is not naturally expressed in wild-type muscle stem cells or muscle cells in general. Typically, the marker protein is a polypeptide that is expressed on the cell surface. Examples of suitable marker proteins include CD8, β-galactosidase, green fluorescent protein, catechol 2,3-dioxygenase, aequorin, and influenza virus hemagglutinin (which can be detected using commercially available monoclonal antibodies); the genes encoding these and other suitable marker proteins are known in the art. Conventional cell sorting methods (e.g., fluorescence-activated cell sorting (FACS)) can be used to isolate those cells in which the Bcl-2 promoter directs the expression of the gene encoding the marker protein. Other techniques, such as the use of protein-conjugated magnetic beads that selectively bind particular cells, also can be used. For example, magnetic beads conjugated to anti-CD8 antibodies can be used to isolate muscle stem cells expressing CD8 under the control of the Bcl-2 promoter.

Included within the invention is a method for producing a population of living cells enriched for muscle stem cells relative to a reference population of cells (i.e., a starting population of cells). This method entails:

(a) providing a reference population of living cells that includes a plurality of muscle stem cells that express Bcl-2 and at least one cell other than a muscle stem cell (e.g., a myoblast); and (b) treating the reference population of cells to induce apoptosis (i.e., programmed cell death) in cells that do not express Bcl-2, thereby producing a population of living cells enriched for muscle stem cells. The expression of Bcl-2 inhibits apoptosis of the muscle stem cells, thereby allowing the muscle stem cells to survive under conditions that result in the death of other cells. In this method, apoptosis can be induced by any of the art-known methods. In a preferred method, the cells are contacted with staurosporine ($C_{28}H_{26}N_4O_3$) in a serum-free cell culture medium. Of course, the surviving muscle stem cells can then be separated from the non-living cells in the cell sample.

The discovery of a molecular marker for muscle stem cells makes it now possible to express an exogenous coding sequence in a muscle stem cell specifically. Thus, the invention also includes a method of expressing an exogenous coding sequence in a muscle stem cell; this method entails:

(a) identifying a myogenic cell as a muscle stem cell;

(b) introducing into the muscle stem cell a genetic construct comprising an exogenous coding sequence operably linked to a muscle stem cell-active promoter, to produce a transfected muscle stem cell; and (c) maintaining the transfected muscle stem cell containing the genetic construct under conditions permitting expression of the exogenous coding sequence. The above-described methods for identifying and/or isolating muscle stem cells by detecting or exploiting the activity of a Bcl-2 promoter can be used in this aspect of the invention.

Preferably, the genetic construct includes a viral vector (i.e., all or a portion of a viral genome). In addition, the genetic construct typically contains a promoter that is active in muscle stem cells (e.g., a Bcl-2 promoter) and which is operably linked to the exogenous gene.

The genetic construct can be introduced into the muscle stem cell in vitro or in vivo. If desired, once a genetic construct has been introduced into a muscle stem cell, the cell subsequently can be introduced into a mammal (e.g., a human or mouse) and maintained under conditions such that the exogenous coding sequence is expressed in the mammal.

The term "Bcl-2" is used herein in accordance with its ordinary definition in the art. The Bcl-2 protein is considered to be an apoptosis-inhibiting, membrane-associated cytoplasmic protein having a molecular weight approximately 26 kD (Tsujimoto et al., 1987, Oncogene 2:3; see also U.S. Pat. Nos. 5,202,429 and 5,015,568). A nucleotide sequence encoding Bcl-2 has been described (Tsujimoto and Croce, 1986, Proc. Natl. Acad. Sci. 83:5214-5218 and GenBank Accession number M13994 under the locus identification HUMBCL2A). A further description of Bcl-2 is provided by Korsmeyer (1995, Trends in Genet. 11:101-105). Preferably, the Bcl-2 protein is a human protein, although Bcl-2 proteins from other species (e.g., mice) also can be used.

By "muscle stem cell" is meant a self-renewing mononucleate cell that produces as progeny mononucleate myoblasts, which are committed to form multinucleate myofibers via intercellular fusion. Encompassed by the invention are muscle stem cells that produce skeletal muscle, smooth muscle, or cardiac muscle.

"Myogenic" cells as described herein are those cells that are related to the origin of muscle cells or fibers. Various molecular markers are known to be specific for the middle and late stages of myogenic differentiation. For example, in C2C12 cells, myosin and MRF4 mark the late stages of myogenesis and are largely restricted to myotubes, whereas myogenin and nestin mark the middle stages of myogenesis and are found in all myotubes and in many committed myoblasts.

By "promoter" is meant a minimal nucleotide sequence sufficient to direct transcription of a coding sequence. Included within the invention are those promoters which are inducible by external signals or agents; such elements can be located in the 5' or 3' untranslated regions of the native gene. A "Bcl-2 promoter" is any sequence contained within the untranslated region of the endogenous Bcl-2 gene that is sufficient to direct transcription of Bcl-2 in muscle stem cells, and which does not direct expression of Bcl-2 in myoblasts or myotubes. For example, a 1.8 kb sequence immediately adjacent to the Bcl-2 transcription start site is sufficient to direct gene expression in muscle stem cells but not myoblasts or myotubes. It is recognized that, in producing genetic constructs containing a Bcl-2 promoter (e.g., those constructs that also contain a reporter gene or a gene encoding a marker protein), minor variations (e.g., deletions, point mutations, and the like) can be made in the sequence of the Bcl-2 promoter without abrogating its ability to be active in muscle stem cells and inactive in other myogenic cells. Thus, Bcl-2 promoters having such minor variations without abrogating the muscle stem cell specificity of the promoter are encompassed by the term "Bcl-2 promoter." In addition, multiple copies of the Bcl-2 promoter, arranged in tandem, can be used to direct gene expression.

By "operably linked" is meant that a coding sequence and a regulatory sequence(s) (e.g., a promoter) are connected in such a way as to permit gene expression when the appropriate molecules (e.g., transcriptional activator proteins) are bound to the regulatory sequence(s).

The term "exogenous" refers to any coding sequence, promoter, polypeptide or other molecule that is supplied to the muscle stem cell (e.g., as part of a genetic construct). Included are those coding sequences that normally are present in the muscle stem cell as well as coding sequences that are not normally present in the muscle stem cell into which the genetic construct is introduced (e.g., related and unrelated genes of other cells or species).

The term "heterologous" refers to any gene, promoter, polypeptide or other molecule that is not naturally present in a wild-type version of a referenced cell. For example, an *E. coli* β-galactosidase gene is considered to be "heterologous" to a human muscle stem cell.

The term "reporter gene" refers to any gene for which gene expression can be monitored. Commonly used reporter genes include, for example, genes encoding chloramphenicol acetyltransferase, alkaline phosphatase, luciferase, and green fluorescent protein.

By "differentiation" is meant the developmental process whereby cells become specialized, i.e., acquire one or more characteristics or functions different from that of the original cell type.

By "proliferation" is meant an increase in number of cells.

By "marker protein" is meant a polypeptide that distinguishes one cell (or set of cells) from another cell (or set of cells) in a population of cells. For example, a polypeptide that is expressed (e.g., by genetic engineering) on the surface of muscle stem cells but not other cells of a cell population serves as a marker protein for the muscle stem cells. Typically, the marker protein is a cell-surface antigen, such that antibodies that specifically bind the marker protein can be used in cell sorting methods, e.g., to produce a population of cells enriched for cells that express the marker protein. Alternatively, intracellular proteins can be used as marker proteins. For example, fluorescent or luminescent proteins, such as green fluorescent protein and aequorin of Aequoria victoria (Tanahashi et al., Gene 96:249–255 (1990)) can be used as the marker protein and can facilitate cell sorting, e.g., by FACS. Also, enzymes can be used, provided that the activity of the enzyme can be detected. For example, β-galactosidase is well suited for use as a marker protein; this enzyme can be detected by introducing into the cell a substrate(s) that releases a fluorescent product(s) upon cleavage by the enzyme (available from, e.g., Molecular Probes). Another suitable enzyme is catechol 2,3-dioxygenase, which is encoded by xylE of *Pseudomonas putida* (Domen et al., Analy. Biochem. 155:379–384 (1986)).

By "apoptosis" is meant the physiological process known as programmed cell death. Unlike other forms of cell death that occur, apoptosis is an active, ATP-requiring form of cell death that typically requires new RNA and protein synthesis. Generally, apoptosis is characterized by the activation of endogenous endonucleases that degrade genomic DNA.

The invention offers the advantage of providing a convenient molecular marker for muscle stem cells. Now that such a marker has been identified, muscle stem cells can readily be isolated from, and/or characterized in, a mixed population of cells. Also, muscle stem cells, as distinct from myoblasts and myofibers, now can be used selectively to express an exogenous gene. These muscle stem cells are expected to be more effective in gene therapy methods than other muscle cells.

Other features and advantages of the invention will be apparent from the following detailed description, and from the claims.

BRIEF DESCRIPTION OF THE DRAWINGS

FIG. 2A shows that the number of viable C2C12 cells, as measured by MTT assay of mitochondrial function, was greatly reduced in serum-free medium (SF) or serum-free medium with 0.5 μM staurosporine (STS) compared to growth medium (GM) or low serum differentiation medium (2% HS). FIG. 2B shows that the percentage of C2C12 cells which expressed Bcl-2 was greater after incubation in serum-free medium with (STS) or without (SF) staurosporine than in control cultures that were maintained in serum-containing media (GM or 2% HS as in FIG. 2A).

DETAILED DESCRIPTION

Identification of a Muscle Stem Cell

Figures 1A, 1B:
FIGS. 1A–1F are a series of photographs from experiments showing that Bcl-2 is expressed in myogenic cultures by a small subset of mononucleate cells (closed arrows), but not myotubes (open arrows). Bcl-2 was detected by immunostaining (FIGS. 1A and 1C) and phase contrast microscopy (FIGS. 1B and 1D) of C2C12 (FIGS. 1A and 1B) and mouse primary (FIGS. 1C and 1D) myogenic cell cultures. Bar=20 μm. Bcl-2 expression was also detected in immunoblots (FIG. 1E) and by RT-PCR (FIG. 1F). These figures show that the Bcl-2 protein (~26 kD) and mRNA (~7.5 kb) were present in C2C12 myogenic cells and in adult mouse thymus cells. The location of 30 kD marker is indicated. Abbreviations used in the figures are as follows: RT=Reverse transcriptase. GM=growth medium. DM=differentiation medium. $H_2O$=no RNA control.

A cell can be identified as a muscle stem cell by detecting activity of a Bcl-2 promoter within a myogenic cell. Before or after assaying for Bcl-2 activity, a cell can be determined to be myogenic by using conventional criteria and methods, e.g., as described below. To detect the activity of the Bcl-2 promoter, any of a variety of conventional methods for detecting gene expression can be used. For example, one can detect the Bcl-2 protein in a cell (or cell extract) and infer that the Bcl-2 promoter is active in that cell. Standard protein detection methods, such as immunoassays, can be employed. Antibodies that specifically bind Bcl-2 are known in the art and readily available for use in such immunoassays; for example, the hamster monoclonal antibody 3 F11 can be used to specifically bind mouse Bcl-2 (Krajewski et al., Cancer Res. 53:4701–4714 (1993)). Any of a variety of standard immunoassays can be used to detect the Bcl-2 protein. For example, immunostaining, immunoblotting, and ELISAs are suitable for use in the invention. If desired, SDS-PAGE and/or protein purification methods can be used to detect the Bcl-2 protein, but such methods generally are less convenient than immunoassays. Generally, however, any art-recognized method for detecting Bcl-2 can be used.

The activity of the Bcl-2 promoter can be detected by detecting Bcl-2 mRNA in the myogenic cell. Reverse transcriptase-PCR (RT-PCR) is a preferred method for detecting the Bcl-2 mRNA, and such a method is described in further detail below. Other RNA detection methods, e.g., in situ hybridization and northern blotting, also can be used. Because the sequence of the Bcl-2 promoter and coding sequences are publicly known, one can readily use conventional criteria to prepare suitable primers and probes for such methods.

As an alternative to detecting the Bcl-2 protein or mRNA in the cell, Bcl-2 expression can be detected with the use of a reporter gene. In such a method, a genetic construct is prepared in which the reporter gene is operably linked to a Bcl-2 promoter. Expression of the reporter gene then can be detected using art-known methods for the chosen reporter gene. Examples of suitable reporter genes include chloramphenicol acetyltransferase genes, alkaline phosphatase genes, luciferase genes, and green fluorescent protein genes.

In this method, the genetic construct typically is a viral-based vector or a plasmid. Conventional molecular biology techniques can be used to produce such a genetic construct. An example of a suitable plasmid is LB124 (provided by L. Boxer, Stanford Univ.) in which the Bcl-2 promoter directs the expression of a luciferase gene in the context of a pBluescript vector.

In practicing this aspect of the invention, the genetic construct carrying the Bcl-2 promoter and the reporter gene is introduced into a population of cells suspected of containing muscle stem cells (e.g., cells obtained by muscle biopsy). Standard cell transformation methods can be used. Because the Bcl-2 promoter is active in muscle stem cells, but not other myogenic cells, muscle stem cells can be identified by identifying those cells in which the reporter gene is expressed. In one application of this method, Bcl-2 expression can be used as a molecular marker for identifying a stem cell component in muscle tumors (e.g., myoblastomas).

Identification of Compounds That Modulate Cell Differentiation and/or Proliferation To determine whether a test compound modulates cell proliferation and/or differentiation, a cell is identified as a muscle stem cell (e.g., by using one of the above-described methods), and the muscle stem cell (typically in a culture dish containing many cells) is contacted with the test compound(s). Any compound of interest can be used as the test compound in this method. The compound can be contacted with the cells at any desired concentration, and the compound typically will be tested over a wide (e.g., 1,000-fold) range of concentrations. The cells then are monitored for changes in the rates or patterns of proliferation and/or differentiation of the muscle stem cells in order to determine which test compounds modulate proliferation and/or differentiation. Typically, such assays are performed in vitro (e.g., in cell culture), although the muscle stem cell can be contacted with the compound in vivo (the cell can be identified as being a muscle stem cell in vitro after contact with the test compound has occurred).

Production of an Enriched Population of Muscle Stem Cells

The above-described methods for identifying muscle stem cells can readily be modified to provide methods for producing a cell population enriched for muscle stem cells, relative to a reference population of cells. The reference population of cells, i.e., the starting population of cells, contains a mixture of cells including a plurality of muscle stem cells and at least one, and typically many, cells other than the muscle stem cells. For example, the reference cell population may include myoblasts and myofibers. Two examples of methods for producing an enriched population of muscle stem cells are described here.

In the first method, a genetic construct is introduced into cells of the reference population. As described above, conventional gene transfer methods can be used. In this genetic construct, a Bcl-2 promoter directs the expression of a marker protein that is heterologous to wild-type cells of the reference population. Examples of suitable marker proteins include heterologous cell-surface polypeptides and intracellular markers, as discussed above. Alternatively, conventional dominant selectable markers can be used (e.g., neo, gpt, zeo, blast, puro, hygro, bleo, or his). The heterologous marker protein can be a naturally-occurring viral, prokaryotic, or eukaryotic protein, or it can be a hybrid or a synthetic variant of such a protein. Typically, the marker protein is a polypeptide that is expressed on the cell surface, and recombinant DNA techniques for anchoring polypeptides in the cell membrane can be used if desired.

Suitable cell sorting methods (e.g., fluorescence-activated cell sorting (FACS)) are known in the art and can be used in the context of this invention to isolate those cells in which the Bcl-2 promoter directs the expression of the gene encoding the marker protein. For example, a fluorescently-labeled antibody can be used to specifically bind a cell-surface polypeptide used as the heterologous marker. Alternatively, an unlabeled antibody can be used to specifically bind the cell-surface polypeptide, and a second, labeled antibody can be used to specifically bind the first antibody. The fluorescently-tagged muscle stem cells can then be sorted away from other cells in the sample by FACS, for example. Other methods for isolating cells that express a given protein also can be used in the invention. For example, techniques that utilize magnetic beads are now commonly used, and suitable kits are commercially available. Generally, such kits utilize a tagged antibody (e.g., a biotin-tagged antibody) to bind the cell-surface marker protein. The antibody-bound cells then are contacted with a magnetic bead-protein conjugate, where the protein portion of the bead-protein conjugate specifically binds the tagged antibody. For example, a streptavidin-magnetic bead conjugate can be used to bind the biotin-tagged antibody to produce a complex containing the magnetic bead-protein conjugate, the tagged antibody, and the cell expressing the marker protein. Such complexes can be separated from other cells by temporarily adhering the complex to a magnet and separating the adhered cells from the other cells (i.e., a population of cells depleted for muscle stem cells). Magnetic beads that are covalently coupled to a secondary antibody are commercially available (e.g., from Advanced Magnetics, Inc.). Other antibody-based methods for sorting cells also are known in the art and can be used in the invention.

In the second method for producing a population of living cells enriched for muscle stem cells, the reference population of cells is treated to induce apoptosis in cells that do not express Bcl-2. The expression of Bcl-2 inhibits apoptosis of the muscle stem cells, thereby allowing the muscle stem cells to survive under conditions that tend to kill other cells. For example, apoptosis can be induced by growing the reference population of cells in serum-free medium with staurosporine (typically 0.1–100 $\mu$M, preferably 0.3–50 $\mu$M, and most typically approximately 0.5 $\mu$M staurosporine). Other apoptosis-inducing reagents have been described and can be used in the invention. The following apoptosis-inducing reagents are commercially available from Clontech (San Diego, Calif.): actinomycin D, anti-Fas (clone D×2), $C_2$-Ceramide, dexamethasone, fas ligand, etoposide, human tumor necrosis factor-$\alpha$, and vincristin sulfate. Optionally, the cells can be monitored for well-known signs of cell death; 0.5–5 days (usually 1–2) days of incubation in the staurosporine medium will result in apoptosis of a high percentage of the cells that do not express Bcl-2. In practice, the percentage of muscle stem cells in the population can be increased from less than 20% to 50–80% of the cell population by this method. Of course, the surviving muscle stem cells can then be returned to a serum-containing medium that lacks staurosporine.

Expression of an Exogenous Coding Sequence in Muscle Stem Cells

The discovery of a molecular marker for muscle stem cells makes it possible to identify and/or isolate muscle stem cells and express an exogenous coding sequence in those cells. The above-described identification and isolation or enrichment methods are suitable for use in this aspect of the invention. Conventional methods for using genetic constructs to express an exogenous coding sequence of a gene in a myogenic cell are relied upon, provided that the exogenous coding sequence is operably linked to a promoter that is active in muscle stem cells. The muscle stem cell containing the genetic construct then is maintained (i.e., cultured) under conditions such that the exogenous gene is expressed. The cell can be identified as a muscle stem cell either before or after the genetic construct is introduced into the cell. Typically, a population of cells enriched for muscle stem cells will be identified and isolated prior to introduction of the genetic construct into the cells. If desired, however, the stem cells can be allowed to differentiate after introduction of the genetic construct (e.g., by growth in a low-serum medium), and markers of terminal differentiation then can be detected.

A wide variety of genetic constructs are suitable for expressing an exogenous coding sequence in a muscle stem cell. Indeed, most if not all of the art-known genetic constructs for expressing exogenous genes or coding sequences in mammalian cells can be used in the invention, provided that they contain (or are engineered to contain) a promoter that is active in muscle stem cells. Thus, suitable genetic constructs for use in this aspect of the invention include viral vectors that can direct gene expression in mammalian cells, such as those that are derived from retroviruses, adenoviruses, herpes viruses, vaccinia viruses, polio viruses, adeno-associated viruses, canary pox virus, or baculoviruses and the like. If desired, a portion of a viral genome can be used as a viral vector to produce the genetic construct for use in the invention provided that the genetic construct is capable of directing expression of the exogenous coding sequence within the muscle stem cell. Of course, such virus-based genetic constructs typically are engineered such that they lack sequences encoding toxic or undesirable polypeptides. Other suitable means for expressing an exogenous coding sequence in a muscle stem cell include, without limitation, the use of naked DNA, ligand-DNA conjugates, adenovirus-ligand-DNA conjugates, and liposome- or polycation-DNA complexes.

Regardless of which method is used to introduce the exogenous coding sequence of the genetic construct into the cell, the exogenous coding sequence should be operably linked to a promoter that is active (i.e., can direct transcription) in a muscle stem cell. If desired, the ability of any given promoter to direct transcription in a muscle stem cell can readily be ascertained by introducing into a muscle stem cell a genetic construct in which the promoter of interest is operably linked to a reporter gene (e.g., luciferase). Expression of the reporter gene then is detected as an indication that the promoter is active in muscle stem cells. Bcl-2 promoters are suitable for use in this context. Also, nestin and desmin promoters can be used, either alone or in conjunction with the Bcl-2 promoter to express the exogenous coding sequence in the cell.

The genetic construct can be introduced into the muscle stem cell in vitro or in vivo. Subsequently, the muscle stem cell can be introduced into a mammal and maintained under conditions such that the exogenous coding sequence is expressed in the mammal. To this end, conventional transplantation methods can be used and can include, for example, temporary or long-term immunosuppression. Thus, the invention provides a method of therapy whereby a muscle stem cell(s) expressing an exogenous coding sequence is introduced into a mammal (e.g., in a method of gene therapy or to induce an immune response). In an alternative method, a polypeptide encoded by the exogenous coding sequence can be purified from the muscle stem cell(s) cultured in vitro and used for any of a variety of purposes such as therapeutic administration to a mammal or production or purification of antibodies. Artknown protein purification and immunology techniques can be used.

Regardless of whether the muscle stem cell is introduced into a mammal or simply maintained in vitro, a wide variety of exogenous coding sequences are suitable for use in the invention. Typically, the exogenous coding sequence will be mammalian, preferably human, in origin. Non-mammalian coding sequences also are useful (e.g., for use as a reporter gene or to provoke an immune response against a prokaryotic or viral antigen). Where the genetic construct is introduced into a muscle stem cell that is subsequently maintained in a mammal, the exogenous coding sequence is preferably one that corrects or ameliorates a physiological disorder in the mammal (e.g., a gene deficiency disorder). The genetic construct can be engineered such that the polypeptide encoded by the exogenous coding sequence is secreted from the muscle stem cell (e.g., by inclusion of art-known sequences encoding signal peptides for protein secretion). Thus, the muscle stem cells (particularly those that are maintained in vivo) can be used to express secreted proteins, such as growth factors (e.g., erythropoietin and human growth factor). Also useful in this aspect of the invention are coding sequences that are transcribed into RNA molecules for use in RNA decoy, antisense, or ribozyme-based methods of inhibiting gene expression (see, e.g., Yu et al., Gene Therapy 1, 13–26 (1994)).

Working Examples

Before providing the results of several experiments, certain parameters of the experimental methods employed are briefly described.

Cells

C2C12 and Sol8 cells were maintained in growth medium (DMEM with 15% fetal bovine serum, 2 mM L-glutamine, 10 mM HEPES, pH 7.4, and 100 U/ml penicillin) and induced to form myotubes in differentiation medium (growth medium with 2% horse serum in place of fetal bovine serum) (Yaffe et al., Nature 270, 725–727 (1977); Blau et al., Science 230, 758–766 (1985); and Montarras et al., New Biologist 3, 592–600 (1991)). Cells for initial primary cultures were obtained from >6 week old adult CD-1 or C57B1/6 mice (available from Charles River Laboratories). For additional cultures, Bcl-2 (+/−) B6, 129-Bcl2$^{tm1sjk}$ mice were interbred, and the resulting progeny were genotyped and used for cell preparation (Veis et al., Cell 75, 229–240 (1993); these mice are available from Jackson Laboratories). Apoptosis was induced by transferring the cells to serum-free differentiation medium, with or without 0.5 μM staurosporine, and cell viability was measured by the MTT assay of mitochondrial function (Jacobsen et al., EMBO J. 13, 1899–1910 (1994)). Myogenic cells from hind limb muscle of adult and newborn mice were isolated by trypsinization of tissue followed by purification on PERCOLL™ (colloidal polyvinylpyrrolidone coated silica) gradients (Smith et al., Development 117, 1125–1133 (1993)). Populations of cells highly enriched for myogenic cells and containing few non-myogenic cells were collected from the 35–50% PERCOLL™ (colloidal polyvinylpyrrolidone coated silica) interface of 3-step (35%, 50%, 70% Percoll) or 2-step (35%, 50% PERCOLL™) (colloidal polyvinylpyrrolidone coated silica) gradients (Bischoff and Heintz, Dev. Dynamics 201, 41–54 (1994)). In some experiments, non-fractionated cells also were used. Cells were cultured for up to 8 days on an entactin, collagen, laminin (ECL) Matrix (Upstate Biotechnology, Lake Placid, N.Y.) in DMEM with 15% horse serum, 3% chicken embryo extract, 2 mM L-glutamine, 10 mM HEPES pH 7.4, 100 U/ml penicillin, and 1 mM pyruvate. For high density cultures, cells were seeded at 300–5000 cells/cm$^2$, and for clonal cultures plated on the day of isolation at 5–17 cells/cm$^2$. For a comparison of Bcl-2-deficient and wild-type muscle cell growth, a 2-step plating procedure was used to ensure the accuracy of the determination of viable-cell plating density. Cells were plated at high density on the day of isolation, trypsinized from plates within 24 hours, and viable cells (by trypan blue exclusion) were counted and re-seeded at high density (320 cells/cm$^2$) or clonal density (1.7 cells/cm$^2$). Cells plated at clonal density were fixed with paraformaldehyde after 8 days of growth, immunostained for desmin expression, and counted to determine the number of nuclei per colony and fusion index. Cell genotypes were determined after counting. Cell proliferation in high density cultures was monitored over four days by scoring cell density using an inverted phase microscope with field areas calibrated at 10× and 40× magnification. The bulk population doubling time was estimated between 12 and 60 hours after replating during rapid cell growth phase. Statistical analysis was by the appropriate unpaired, two-tailed t-test or non-parametric Mann-Whitney test using InStat (v. 1.12, Graphpad Software, San Diego Calif.).

Bcl-2 Promoter-neo Vector

The Bcl-2 promoter-neo vector was prepared by using HindIII and MluI to excise the RSV promoter of pRSVneo (Gorman et al., Science 221:551–553 (1983)), after which an ~2.6 kb PstI fragment of the human Bcl-2 promoter region (plasmid LB124; Chen et al., Mol. Cell. Biol. 15, 3840–3847 (1995)) was blunt-end ligated to the promotorless neo plasmid. C2C12 cells were transfected with Bcl-2-neo or pSV2neo using LIPOFECTAMINE™ (3:1 (w/w) 2,3-dioleyloxy-N-[2(spermine-carboxamido)ethyl]-N,N-dimethyl-1-propanaminiumtrifluoroacetate and dioleoyl phosphatidylethanolamine) (Gibco-BRL) and selected with G-418 (Dominov et al., Dev. Genet. 19, 108–118 (1996)).

Immunostaining

The hamster mAb, 3 F11, is specific for mouse Bcl-2 (Krajewski et al., Cancer Res. 53, 4701–4714 (1993)) and was used at 25 μg/ml. Mouse mAbs to myosin heavy chain (F59) and myogenin (F5D), and rabbit antisera specific for MyoD, Myf-5 and MRF4 were used as before (Smith et al., Development 117, 1125–1133 (1993); Smith et al., J. Cell Biol. 127, 95–105 (1994); Block et al., Mol. Cell. Biol. 12, 2484–2492 (1992)). A mouse mAb to desmin (Cappel) was used at a 1:40 dilution. Fixed and permeabilized cultures (Smith et al., Development 117: 1125–1133 (1993)) were incubated overnight at room temperature with both a rabbit antiserum and the Bcl-2 mAb; washed four times for 20 minutes each with 0.1% TRITON-X-100™ (t-Octylphenoxylpoly-ethoxyethanol) in PBS; and incubated for 1.5 hours at room temperature with a combination of Texas red- or Cy3-conjugated anti-rabbit IgG (Jackson Immunoresearch) and fluorescein-conjugated anti-hamster IgG (Vector) at 1.0 μg/ml. To double stain for Bcl-2 and antigens detected by mouse mAbs, cultures were incubated sequentially with (i) the mouse mAb; (ii) a lissamine rhodamine-conjugated Fab fragment of goat anti-mouse IgG (Jackson Immunoresearch) at 10 μg/ml; (iii) the hamster anti-Bcl-2 mAb; and (iv) fluorescein-conjugated anti-hamster IgG at 1.0 μg/ml. For each analysis, ≧300 Bcl-2-expressing cells in at least two independent cultures were examined. Bromodeoxyuridine was used at 40 μM and detected with a specific mouse mAb.

Immunoblotting

Cells were scraped into 1 ml of cold PBS and centrifuged at 12,000 rpm for 15 seconds. Cell pellets or adult mouse thymuses were immediately lysed in ~2 volumes of SDS-PAGE sample buffer, boiled for 4 minutes, and analyzed by SDS-PAGE in 15% gels (Kachinsky et al., Dev. Biol. 165:216–228 (1994)). After SDS-PAGE, proteins were electroblotted to a PVDF membrane for 1.5 hours at 75 volts. The transfers were dried for 30 minutes in a vacuum chamber and incubated for 1 hour at room temperature with Bcl-2 mAb at 25 μg/ml in tris-buffered saline with 0.3% TRITON-X-100™ (t-Octylphenoxylpoly-ethoxyethanol) and 1% nonfat dried milk. Antibody binding was visualized using a horseradish peroxidase secondary antibody system (ABC-Elite, Vector) with a chemiluminescent substrate (ECL, Amersham).

RNA Analyses

For RT-PCR, 5 μg of total RNA from C2C12 cells or 0.2 μg poly (A)+RNA from adult mouse brain were reverse transcribed using oligo (dT) primers; and 1/5 of each cDNA product was subjected to PCR (GENEAMP™ (PCR Kit), Perkin Elmer). For mouse Bcl-2, the upstream primer was 5'-AGCCCTGTGCCACCATGTGTC-3' (SEQ ID NO: 1) and the downstream primer was 5'-GGCAGGTTTGTCGACCTCACT-3' (SEQ ID NO: 2). The primers are complementary to sequences in two Bcl-2 exons that are separated by a large intron in genomic DNA. The 480 bp amplified cDNA includes sequences corresponding to the C-terminal 153 amino acids encoded by the ~7.5 kb Bcl-2 mRNA (Negrini et al., Cell 49:455–463 (1987)). PCR conditions were: 94° C. for 5 minutes; 30 cycles of 94° C. for 1 minute; 55° C. for 1 minute; 72° C. for 1 minute; and then 72° C. for 10 minutes. Samples (1/5) of each product were analyzed by Southern blotting using an 865 bp HindIII-EcoRI fragment of mouse Bcl-2 cDNA (plasmid 3027 from S. Korsmeyer) as probe. Northern blots of total RNA (10 μg/lane) from growing and differentiated C2C12 cells were also probed with this cDNA. Hybridizations were as described for RNA blots with final washes in 0.2× SSC, 0.1% SDS, at 65° C. (Bischoff et al., Dev. Dynamics 201, 41–54 (1994)).

PART I

Experiment I

Figures 1C, 1D:
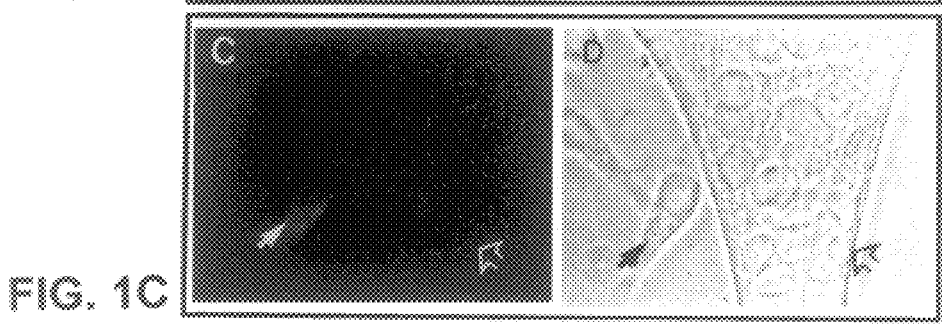
Figures 1E, 1F:
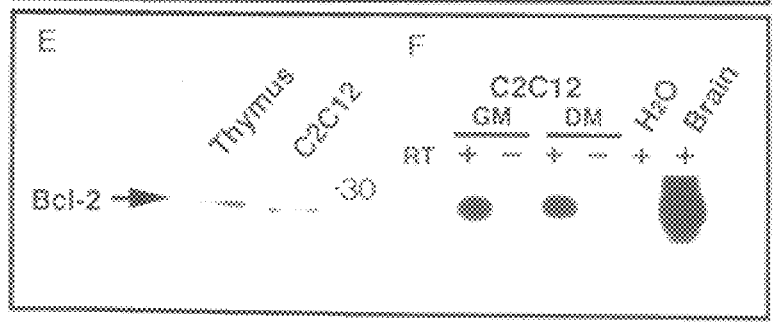

To show that Bcl-2 is expressed in muscle stem cells but not other cells, cells of the C2C12 and Sol8 mouse muscle cell lines were immunostained with a mAb specific for Bcl-2. A small subset of the mononucleate cells showed the punctate cytoplasmic staining indicative of Bcl-2, whereas none of the multinucleate myotubes showed Bcl-2 staining (FIGS. 1A and 1B) (Krajewski et al., Cancer Res. 53, 4701–4714 (1993)). The percentage of Bcl-2-positive cells ranged from ~5–20% for C2C12 cells and from ~3–5% for Sol8 cells. Similarly, Bcl-2 was expressed by a small percentage of mononucleate, but not multinucleate, cells in primary cultures of adult mouse muscle cells (FIGS. 1C and 1D). Furthermore, Bcl-2 was expressed by ~1–4% of the mononucleate cells in clonal muscle colonies formed by the progeny of single adult mouse muscle cells (not shown).

Experiment II

Figures 2A, 2B:
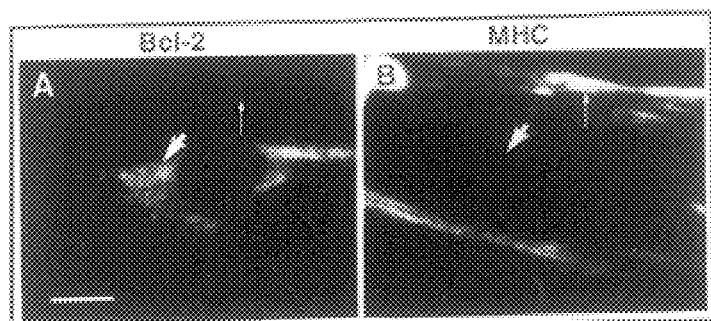
FIGS. 2A–2H are a series of photographs showing the expression patterns of Bcl-2 and several muscle-specific proteins. In growing cultures, the mononucleate C2C12 cells that express Bcl-2 (FIGS. 2A, 2C, 2E, and 2G) did not coexpress myosin (FIG. 2B) or myogenin (FIG. 2D). About 80% of the Bcl-2-positive cells in growing cultures did not express MyoD (FIG. 2F), whereas ~20% of the Bcl-2-positive cells did express MyoD (insets in FIGS. 2E and 2F). Desmin (FIG. 2H) was coexpressed with many, but not all, Bcl-2-positive cells. Closed, downward pointing arrows indicate cells that expressed Bcl-2, but not the other tested protein. Open, downward pointing arrows indicate cells that coexpressed Bcl-2 and the tested protein. Small, upward pointing arrows indicate cells that expressed the tested antigen, but not Bcl-2. Bar=20 μm.
Figures 2C, 2D:
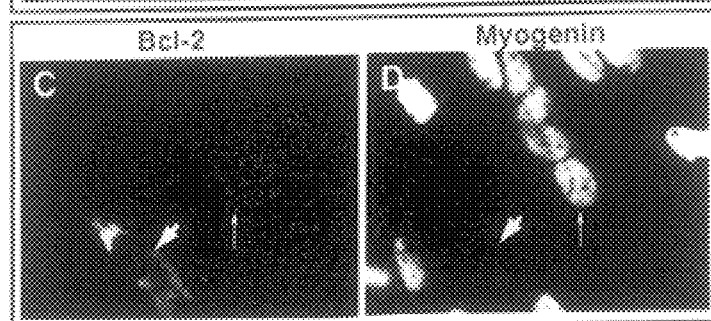
Figures 2E, 2F:
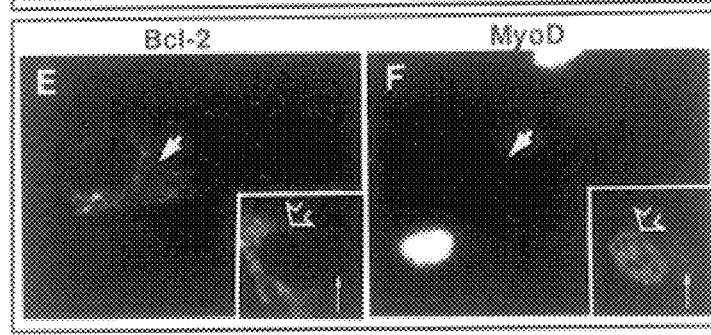

Immunoblotting, northern blotting, and RT-PCR confirmed that myogenic cells expressed Bcl-2 mRNA and protein. On immunoblots probed with anti-Bcl-2 mAbs, lysates of mouse thymus and C2C12 cells showed identical bands of ~26 kD, which is the predicted size for Bcl-2 protein (FIG. 2E) (Haldar et al., Cancer Res. 56, 1253–1255 (1996)). On northern blots of growing and differentiated C2C12 cells, a transcript of ~7.5 kb was detected, which is the predicted size for Bcl-2 (data not shown; Negrini et al., Cell 49, 455–463 (1987)). When using mRNAs from both adult mouse brain, in which Bcl-2 is expressed (Negrini et al., Cell 49, 455–463 (1987)), and C2C12 cells, RT-PCR produced a single cDNA that was the expected size (480 bp) for Bcl-2 and which hybridized to a Bcl-2 probe (FIG. 2F).

Experiment III

A comparison of the expression patterns of Bcl-2 and several muscle-specific proteins showed that Bcl-2-positive C2C12 cells are at a very early stage of myogenic differentiation. For instance, Bcl-2 was not coexpressed with markers specific for the middle and late stages of myogenic differentiation. Upon examining ≧300 Bcl-2-positive cells for each marker, no individual cells were found in which Bcl-2 was coexpressed with myosin, myogenin, MRF4, or nestin (FIGS. 2A–2D and not shown). Myosin and MRF4 mark late stages of C2C12 myogenesis and are largely restricted to myotubes, whereas myogenin and nestin mark middle stages of myogenesis and are found in many committed myoblasts, as well as in all myotubes (Miller, J. Cell Biol. 111, 1149–1160 (1990); Kachinsky et al., Dev. Biol. 165, 216–228 (1994)).

Figures 2G, 2H:
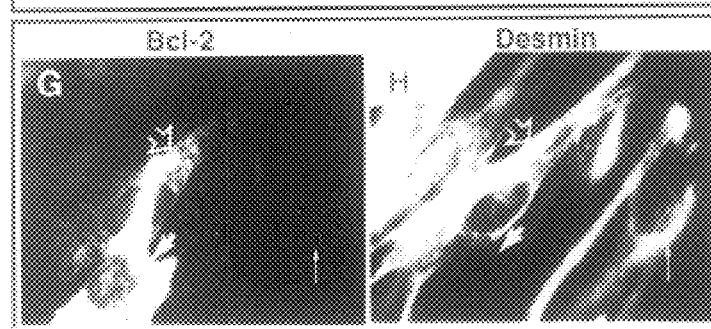

Coexpression of Bcl-2 with three markers of early myogenesis was also examined. These markers were Myf-5, MyoD, and desmin (Smith et al., Development 117, 1125–1133 (1993); George-Weinstein et al., Dev. Biol. 156, 209–229 (1993)). As C2C12 cultures approached confluence in growth medium, ~80% of the Bcl-2-expressing cells did not express either MyoD or Myf-5 (FIGS. 2E and 2F and not shown); whereas ~20% of the Bcl-2-positive cells did express MyoD or Myf-5 (insets FIGS. 2E and 2F and not shown). When cultures were switched to differentiation medium, the percentage of Bcl-2-positive cells that coexpressed either MyoD or Myf-5 decreased rapidly until, after four days in low serum medium, neither MyoD nor Myf-5 was expressed in any of the Bcl-2-positive cells. Desmin was expressed by ~85% of the Bcl-2-positive C2C12 cells as cultures neared confluence in growth medium (FIGS. 2G and 2H), but by only ~20% of the Bcl-2-positive cells after two days in differentiation medium (not shown). In addition, desmin was coexpressed with most Bcl-2-positive cells in mouse primary muscle cell cultures, including the Bcl-2-positive cell in FIG. 1C, confirming that these cells were myogenic (George-Weinstein et al., Dev. Biol. 156, 209–229 (1993)).

In growing cultures nearing confluence, ~25% of the Bcl-2-positive and ~35% of the Bcl-2-negative C2C12 cells incorporated bromodeoxyuridine during a one day incubation, and thus appeared capable of cell division (not shown). These patterns of muscle gene expression indicate that, as Bcl-2-positive cells and their progeny differentiate, Bcl-2 and desmin initially become coexpressed, but Bcl-2 expression stops as first Myf-5 and MyoD and then later markers of terminal differentiation are expressed.

Experiment IV

Figure 3A:
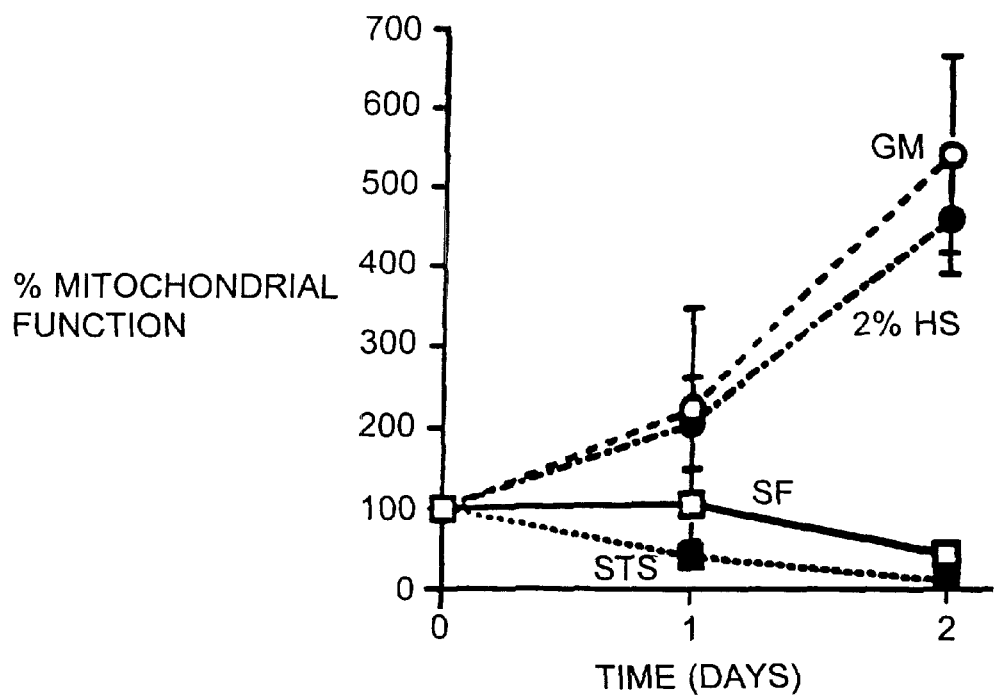
FIGS. 3A and 3B are a pair of graphs representing cell viability in myogenic cultures grown various media.
Figure 3B:
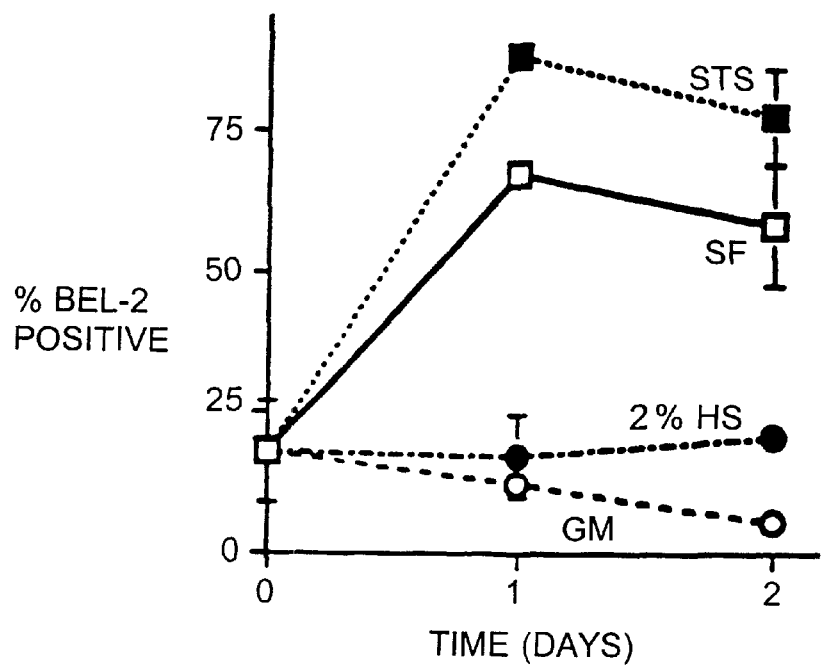

In this experiment, apoptosis was induced and Bcl-2 expression, cell viability, and differentiation capability were examined in cultures of myogenic cells. Because serum-free medium and staurosporine (a protein kinase inhibitor) induce apoptosis in many types of cells (including Sol8 cells), growing C2C12 cells were switched into one of three media: (i) differentiation medium with 2% horse serum, (ii) serum-free medium, or (iii) serum-free medium with 0.5 μM staurosporine (Jacobsen et al., EMBO J. 13, 1899–1910 (1994); Jacobsen et al., J. Cell Biol. 133, 1041–1051 (1996); Mampuru et al., Exp. Cell Res. 226, 372–380 (1996)). At 1–2 days after the switch, the number of viable cells, measured by mitochondrial function (Jacobsen et al., EMBO J. 13, 1899–1910 (1994)), had decreased in serum-free cultures, but had increased in serum-containing cultures (FIG. 3A). Pyknotic nuclei, which indicate apoptotic cells (Korsmeyer, Trends Genet. 11, 101–105 (1995); Jacobsen et al., EMBO J. 13, 1899–1910 (1994)), were abundant in serum-free cultures after 1–2 days, but rare in serum-containing cultures (not shown). The percentage of C2C12 cells that expressed Bcl-2 remained at <20% in serum-containing cultures, but was significantly (P<0.01) increased to 50–80% after two days in serum-free culture (FIG. 3B). Muscle cells, in common with many other cell types (Korsmeyer, supra), thus appear less likely to undergo apoptosis when expressing Bcl-2. Stem cells were inferred to have been included among the C2C12 cells that survived serum-free medium and staurosporine because surviving cells were able to proliferate and carry out all stages of myogenesis, including myotube formation, when returned to serum-containing media (not shown).

Experiment V

Figure 4:
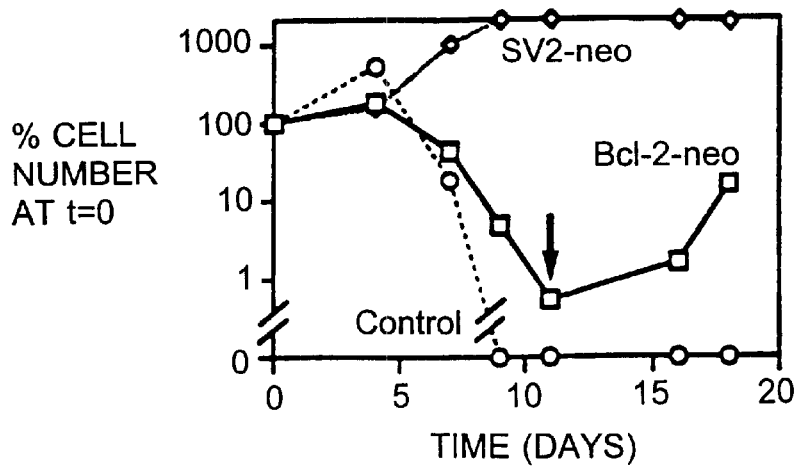
FIG. 4 is a graph showing that a portion of C2C12 cells that carry a Bcl-2 promoter-neo fusion gene (Bcl-2-neo) survived 11 days of selection in 500 μg/ml G-418 whereas the same treatment killed all untransfected C2C12 cells (control) and had no effect on C2C12 cells that carried the neo gene under control of the ubiquitously expressed SV40 promoter (pSV2neo). When the G-418-containing medium was replaced after 11 days with normal growth medium (arrow), Bcl-2-neo cells resumed proliferation.

To determine whether Bcl-2-expressing cells could function as stem cells, the differentiation of modified C2C12 cells that were selected based on their ability to express a Bcl-2 promoter fragment was examined. C2C12 cells were transfected with a plasmid in which expression of neomycin phosphotransferase was under the control of an ~2.6 kb fragment of the human Bcl-2 promoter (Chen and Boxer, Mol. Cell. Biol. 15, 3840–3847 (1995)). From these transfections, four independent G-418-resistant lines (termed Bcl-2-neo cells) were isolated. Transfection of a control plasmid lacking only the Bcl-2 promoter did not produce G-418-resistant cells. For each Bcl-2-neo line, as shown for one experiment in FIG. 4, a portion of the cells remained viable after culture for 11 days in growth medium containing 500 μg/ml G-418. In contrast, this treatment killed all untransfected C2C12 control cells and had no effect on C2C12 cells transfected with the ubiquitously expressed pSV2neo (FIG. 4). When transferred to fresh growth medium without G-418, the selected Bcl-2-neo cells resumed proliferation (FIG. 4) and were able to form multinucleate myotubes when switched to differentiation medium at confluence (not shown).

A second round of G-418 selection produced the same result: only a portion of the Bcl-2-neo cells survived selection, yet the doubly selected cells remained capable of forming myotubes. Furthermore, in differentiated cultures of G-418-selected Bcl-2-neo cells, as in control cells, Bcl-2 was expressed in a small percentage of the mononucleate, but not multinucleate, cells and was not coexpressed with myogenin or MHC (not shown). Thus, cells that expressed the Bcl-2 promoter fragment and became G-418-resistant were able—as expected for muscle stem cells—to generate the different phenotypes of myogenic cells found in control C2C12 cultures.

PART II

To further characterize the activity of the Bcl-2 promoter, the molecular marker protein CD8 was expressed under the control of the Bcl-2 promoter.

Experiment VI

Bcl-2 promoter-CD8 vector

To provide further evidence that the Bcl-2 promoter directs gene expression in muscle stem cells, a plasmid was obtained in which expression of luciferase is driven by an ~2.5 kb fragment of the human Bcl-2 promoter (Chen and Boxer, Mol. Cell. Biol. 15, 3840–3847 (1995)). The luciferase coding sequence was replaced with cDNA encoding the cell surface protein CD8 (cDNA obtained from the American Type Culture Collection). After stable transfection of C2C12 cells, one line was obtained in which CD8 is expressed. In immunohistology experiments using an anti-CD8 mAb (obtained from Dynal Corp., Oslo, Norway), the clonal line was tested. A small proportion (~15%) of the mononucleate cells, but none of the myotubes, expressed CD8. This observation, along with the observations with the Bcl-2-neo cells described above in Experiment V, indicate that the human Bcl-2 promoter fragment drives expression of CD8 in the small subset of mouse muscle mononucleate cells.

Experiment VII

To provide further evidence that the Bcl-2 promoter is active in muscle stem cells, anti-CD8 magnetic beads (Dynal Corp.) were used to purify the fraction of the stably transfected cells that expressed CD8 under the control of the Bcl-2 promoter. After purification with the magnetic beads, the percentage of CD8-expressing cells was increased from about 15% to >95%. These bead-selected cells retained the characteristics of stem cells, including the ability to form committed myoblasts and myotubes.

Experiment VIII

Finally, it was reasoned that if Bcl-2 is a marker for muscle stem cells, muscle cells that lack Bcl-2 (i.e., Bcl-2 (−/−) cells) should be deficient in producing muscle colonies upon cloning. Indeed, muscle cells that lack Bcl-2 produce myotubes, but form smaller muscle colonies than do wild-type cells (Bcl-2 (+/+) cells). In this experiment, the myogenic capabilities of cells obtained from the limbs of newborn Bcl-2 (−/−) mice were compared with those obtained from wild-type littermates. In high density cultures, Bcl-2-deficient and wild-type cells had similar rates of cell proliferation in growth medium, with population doubling times of ~10 hours and no differences in myotube formation.

For clonal analyses, cells were cultured at clonal density and allowed eight days to form muscle colonies. Independent clonal cultures were established from three Bcl-2-deficient newborns and four wild-type newborns from two litters. Cultures were stained for desmin to distinguish muscle colonies (which are desmin-positive) from non-muscle colonies (which are desmin-negative). Muscle colonies were examined to determine both the total number of nuclei in the colony and the percentage of nuclei in myotubes.

Figure 5:
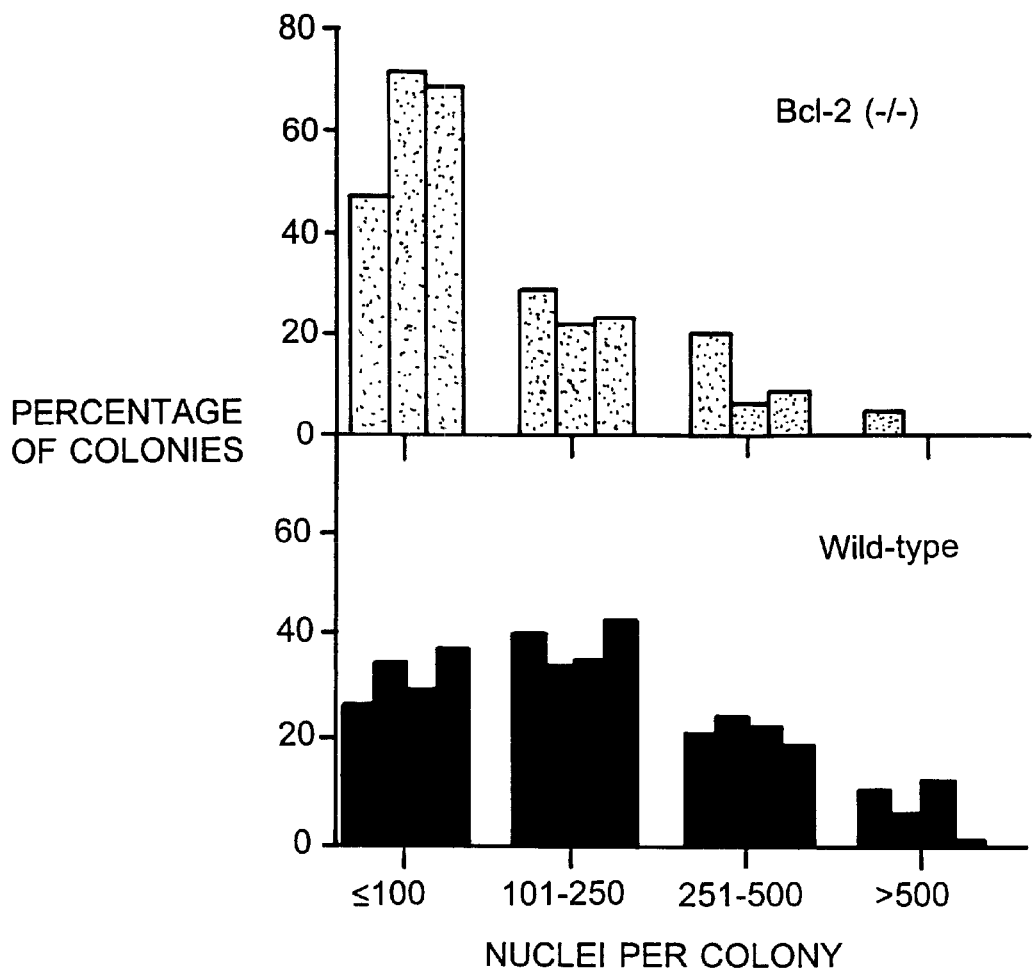
FIG. 5 is a pair of histograms showing that, when cloned, Bcl-2-deficient cells produce smaller muscle colonies than do wild-type cells. Clonal cultures were established from individual newborn mice (n=3 for Bcl-2-deficient, and n=4 for wild-type), and the number of nuclei in each resulting muscle colony was determined. Colony sizes from each individual were grouped into one of four bins (≦100, 101–250, 251–500, or >500 nuclei), and graphed with the four points obtained from each individual in the same relative position (e.g., the four left-most bars were from a single individual). Most of the muscle colonies produced from Bcl-2-deficient cells contained fewer than 100 nuclei (upper panel). In contrast, the size distribution of muscle colonies produced from wild-type cells was shifted to larger sizes, so that most wild-type colonies contained more than 100 nuclei (lower panel).
Figure 6:
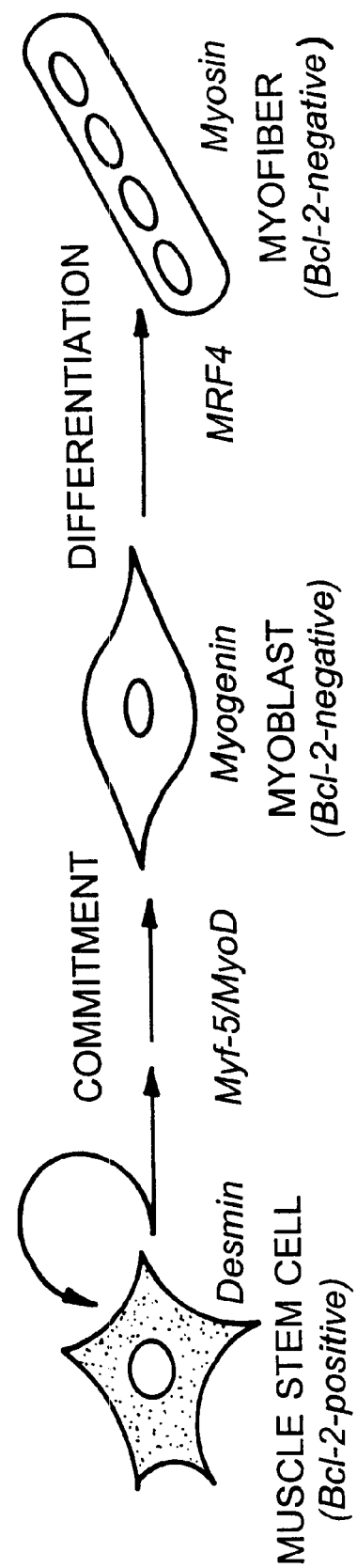
FIG. 6 is a schematic representation of the stages in the myogenic cell lineage, including the expression patterns of Bcl-2 and additional marker genes. Bcl-2 expression precedes expression of the indicated marker genes. Note also that Bcl-2 expression stops prior to myoblast commitment, whereas expression of each of the other markers continues into the myofiber stage of differentiation.

Muscle colonies formed from Bcl-2(−/−) cells contained an average±SE of 112.6±9.7 nuclei (n=178), whereas muscle colonies formed from wild-type cells contained an average±SE of 202.8±11.8 nuclei (n=274), which is a highly significant ($P<0.0001$) difference. Both Bcl-2-deficient and wild-type cells produced colonies with a wide range of nuclear number, although Bcl-2-deficient cells produced relatively more small colonies and relatively fewer large colonies than wild-type cells (FIG. 5). In contrast to the differences in colony size, fusion indices and cloning efficiencies were similar for Bcl-2-deficient and wild-type cells. The average percentage of nuclei within myotubes was 24.9±13% for cells without Bcl-2 and 22.3±0.9% for wild-type cells. The percentage of cloned cells that formed muscle colonies ranged, in different experiments, from ~20–40% for both Bcl-2-deficient and wild-type cells. The colony formation assays show that Bcl-2-deficient muscle cells produce smaller muscle colonies than do wild-type cells, indicating that Bcl-2 plays a necessary role in the clonal expansion of muscle colony-forming cells in newborn mice. A role for Bcl-2 in muscle clonal expansion also is predicted from the restricted expression pattern of Bcl-2 in early stage muscle cells, since it is the early-stage cells (i.e., cells prior to commitment) that are progenitors of muscle colonies. FIG. 6 is a diagram illustrating how expression of Bcl-2 differs from expression of other muscle proteins, and thus serves as a molecular marker for muscle stem cells.

Summary

The experiments described above demonstrate that Bcl-2 is a molecular marker for muscle stem cells. Thus, muscle stem cells now can readily be distinguished and isolated from other myogenic cells.

Other embodiments are within the following claims.

What is claimed is:

1. A method for identifying a muscle stem cell, the method comprising providing a sample comprising a myogenic cell, and detecting expression of a sequence operatively linked to a Bcl-2 promoter within the myogenic cell as an indication that the myogenic cell is a muscle stem cell.

2. The method of claim 1, wherein expression is detected by detecting Bcl-2 mRNA in the myogenic cell.

3. The method of claim 1, wherein expression is detected by detecting a Bcl-2 protein in the myogenic cell.

4. The method of claim 3, wherein the Bcl-2 protein is detected in an immunoassay.

5. The method of claim 1, wherein the Bcl-2 promoter is operably linked to a heterologous reporter coding sequence.

6. The method of claim 5, wherein expression is detected by detecting a polypeptide encoded by the heterologous reporter coding sequence.

7. A method for determining whether a test compound modulates muscle stem cell differentiation, the method comprising:
   (a) providing a muscle stem cell;
   (b) contacting the muscle stem cell with the test compound; and
   (c) detecting a change in the rate or pattern of differentiation of the muscle stem cell as an indication that the test compound modulates muscle stem cell differentiation.

8. The method of claim 7, wherein the muscle stem cell is identified as a muscle stem cell by detecting expression of a Bcl-2 protein in the muscle stem cell.

9. A method for determining whether a test compound modulates the rate of muscle stem cell proliferation, the method comprising:
 (a) providing a muscle stem cell;
 (b) contacting the muscle stem cell with the test compound; and
 (c) detecting a change in the rate of proliferation of the muscle stem cell as an indication that the test compound modulates the rate of muscle stem cell proliferation.

10. The method of claim 9, wherein the muscle stem cell is identified as a muscle stem cell by detecting expression of a Bcl-2 protein in the muscle stem cell.

11. A method for producing a popultion of cells enriched for muscle stem cells relative to a reference population, the method comprising:
 (a) providing a reference population of cells comprising a plurality of muscle stem cells and at least one cell other than a muscle stem cell,
 (b) introducing into the reference population of cells a genetic construct comprising a Bcl-2 promoter operabled linked to a gene encoding a marker protein that is heterologous to wild-type cells of the reference population, thereby producing a transfected population of cells, and
 (c) selecting from the transfected population of cells those cells that express the marker protein, thereby producing a population of cells enriched for muscle stem cells.

12. The method of claim 11, wherein the marker protein is a cell surface polypeptide.

13. The method of claim 11, wherein the marker protein is selected-from the group consisting of CD8, influenza virus hemagglutinin, β-galactosidase, green fluorescent protein, catecol 2,3-dioxygenase, and aequorin.

14. A method of modulating differentiation in a population of cells enriched for muscle stem cells, the method comprising:
 (a) providing a population of cells enriched for muscle stem cells, wherein the population is produced by the method of claim 11,
 (b) contacting at least a portion of the population of cells with a test compound to produce a treated population of cells, and
 (c) detecting a change in the rate or pattern of differentiation of a muscle stem cell cbitained within the treated population of cells as an indication that the test compound modulates differentiation in a population of cells enriched for muscle stem cells.

15. A method for producing a population of living cells enriched for muscle stem cells relative to a reference population of cells, the method comprising:
 (a) providing a reference population of living cells comprising a plurality of muscle stem cells that express Bcl-2 and at least one cell other than a muscle stem cell, and
 (b) treating the reference population of cells to induce apoptosis in cells that do not express Bcl-2, thereby producing a population of living cells enriched for muscle stem cells.

16. The method of claim 15, wherein the treatment comprises contacting the reference population of cells with staurosporine and serum-free medium.

17. A method of modulating differentiation in a population of cells enriched for muscle stem cells, the method comprising:
 (a) providing a population of cells enriched for muscle stem cells, wherein the population is produced by the method of claim 15,
 (b) contacting at least a portion of the population of living cells enriched for muscle stem cells with a test compound to produce a treated population of cells, and
 (c) detecting a change in the rate or pattern of differentiation of a muscle stem cell contained with the treated population of living cells as an indication that the test compound modulates differentiation in a population of cells enriched for muscle stem cells.

* * * * *